United States Patent [19]

Yovankin

[11] 4,424,809

[45] Jan. 10, 1984

[54] KNEE BANDAGE

[75] Inventor: Robert A. Yovankin, Medford, N.J.

[73] Assignee: KCP Bandage, Inc., Pennsauken, N.J.

[21] Appl. No.: 364,044

[22] Filed: Mar. 31, 1982

[51] Int. Cl.³ ............................................. A61F 13/00
[52] U.S. Cl. ........................................ 128/165; 54/82
[58] Field of Search ............... 128/80 C, 80 R, 165, 128/87, 82, 402; 119/126, 127; 54/82

[56] References Cited

U.S. PATENT DOCUMENTS

| 144,315 | 11/1873 | Cooper. | |
|---|---|---|---|
| 2,937,487 | 5/1960 | Dever | 54/82 |
| 3,209,516 | 4/1965 | Hyman | 54/82 |
| 3,717,145 | 2/1973 | Berndt et al. | 128/402 |
| 3,831,467 | 8/1974 | Moore | 128/80 C |
| 4,013,070 | 3/1977 | Harroff | 128/80 C |
| 4,099,269 | 7/1978 | Porner | 54/82 |
| 4,116,236 | 9/1978 | Albert | 128/80 C |
| 4,140,116 | 2/1979 | Hampicke | 128/165 |
| 4,342,185 | 8/1982 | Pellew | 54/82 |

Primary Examiner—John D. Yasko
Attorney, Agent, or Firm—Seidel, Gonda & Goldhammer

[57] ABSTRACT

An enclosure of stretch fabric has stitching defining a plurality of parallel elongated pockets each containing a pad of foam plastic having a length of about 30-35 millimeters. The pads adapted to be on the inner and outer sides of the knee as well as the pads adapted to be adjacent a rear surface of the knee have a zone of reduced cross-sectional area. Straps are provided to apply the bandage to the knee of a horse.

9 Claims, 6 Drawing Figures

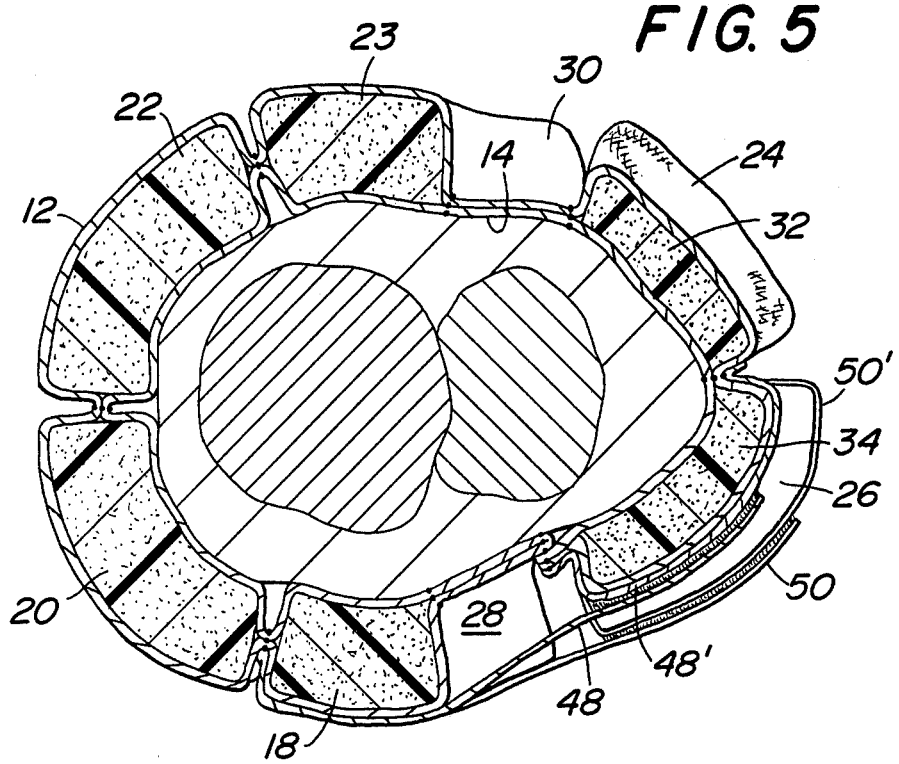
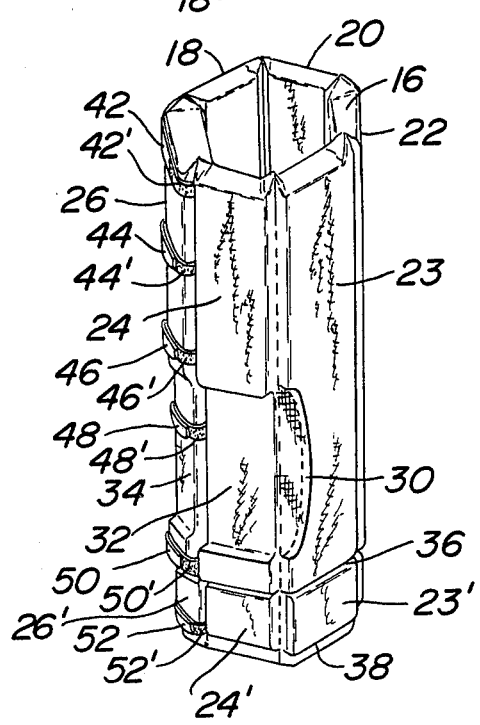

KNEE BANDAGE

BACKGROUND

A knee brace having resilient pads is taught by U.S. Pat. No. 4,116,236. A knee bandage having foam pads and which adapted to be attached by way of Velcro (trademark) strips is taught by U.S. Pat. Nos. 3,831,467 and 4,013,070. A hock protector for a horse is taught by U.S. Pat. No. 3,209,516. Bandages having pockets for receiving medication is taught by U.S. Pat. No. 144,315.

While a wide variety of bandages have been proposed heretofore, they are deficient in one or more respects. There is a need for a horse knee bandage which can be applied quickly while standing along side the horses to minimize danger to the person applying the same. The bandage should be designed so that it can overlie the upper end of a standing bandage, poultice plaster on the knee, oil rubbed onto the knee to create sweat, or a cool pack. At the same time, the bandage should not be capable of restricting circulation. The knee bandage of the present invention is designed to have those features.

SUMMARY OF THE INVENTION

The knee bandage of the present invention is directed to an enclosure of stretch fabric having stitching defining a plurality of parallel elongated pockets. A pad of foam plastic is provided in each pocket. Each pad has a length of about 30-35 millimeters. The pads adapted to be on opposite sides of a knee have a zone of reduced cross-sectional area. At least one of the pads adapted to be adjacent a rear surface of the knee has a zone of reduced cross-sectional area. A plurality of straps are attached along one side edge portion of the bandage for mating with strap loops along the opposite side edge portion of the bandage.

It is an object of the present invention to provide a novel knee bandage for animals such as horses.

It is another object of the present invention to provide a knee bandage which does not interfere with circulation or mobility.

It is another object of the present invention to provide a knee bandage for the front legs of a horse in a manner so that the bandage may overlie conventional treatments applied to a knee of a horse.

Other objects and advantages will appear hereinafter.

For the purpose of illustrating the invention, there is provided in the drawing a form which is presently preferred: it being understood, however, that this invention is not limited to the precise arrangements and instrumentalities shown.

FIG. 5 is a sectional view taken along the line 5—5 in FIG. 3.

FIG. 6 is a perspective view of the bandage in a closed disposition.

DETAILED DESCRIPTION

Figure 1:
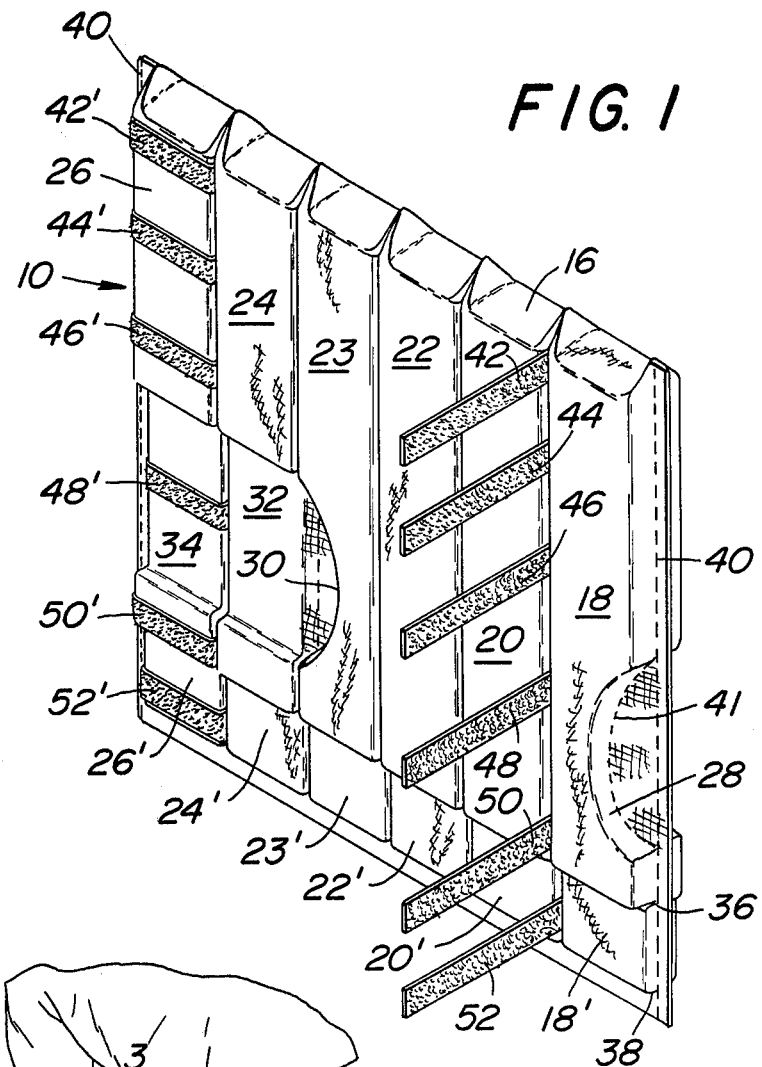
FIG. 1 is a perspective view of a bandage in accord with the present invention.
Figure 2:
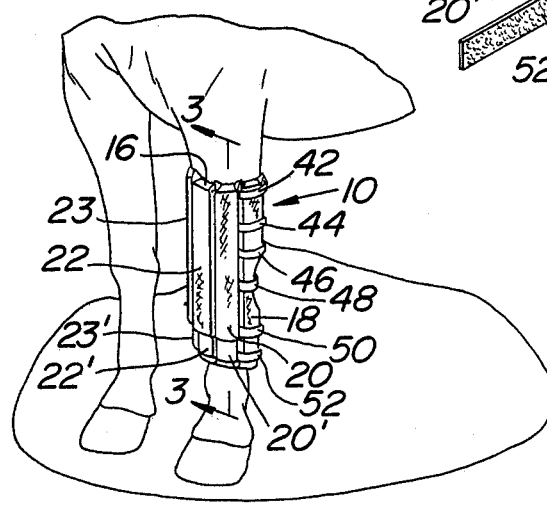
FIG. 2 is a partial perspective view of the front end of a horse with the bandage applied to the knee of the left foot.

Referring to the drawing, in detail, wherein like numerals indicate like elements, there is shown a knee bandage in accordance with the present invention designated generally as 10. The bandage 10 includes an enclosure of stretch fabric having an outer panel 12 and an inner panel 14 connected together at the bight 16 which occurs at the upper end of the bandage. The panels 12 and 14 are stiched together to provide a plurality of elongated vertical pockets. Each pocket receives a pad of foam plastic having a length of 30-35 millimeters.

The foam plastic pads are designated 18, 20, 22, 23, 24 and 26. Each pad is of the same length, width and thickness except as will be made clear hereinafter. The stitching joining the front and rear panels between the adjacent pads is shown more clearly in FIG. 5.

As shown more clearly in FIG. 5, panels 20 and 22 overlie the knee cap. Panels 18 and 23 overlie a side of the knee and therefore are generally oppositely disposed. Pads 24 and 26 overlie the rear surface behind the knee.

A zone of pad 18 is provided with a notch 28 which is generally semicircular. A similar notch 30 is provided on the pad 23. Thus, the pads on opposite sides of the knee are notched with the notch facing rearwardly as will be apparent from FIG. 5. Pads 24 and 26 are provided with a reduced thickness portion 32 and 34 respectively. Thus, each of pads 18, 23, 24 and 26 has a zone of reduced cross-sectional area with the zones being coextensive. When the knee is flexed, part of the reduced thickness portion 34 is deformed into notch 28 and part of reduced thickness portion 32 is deformed into notch 30.

Figure 3:
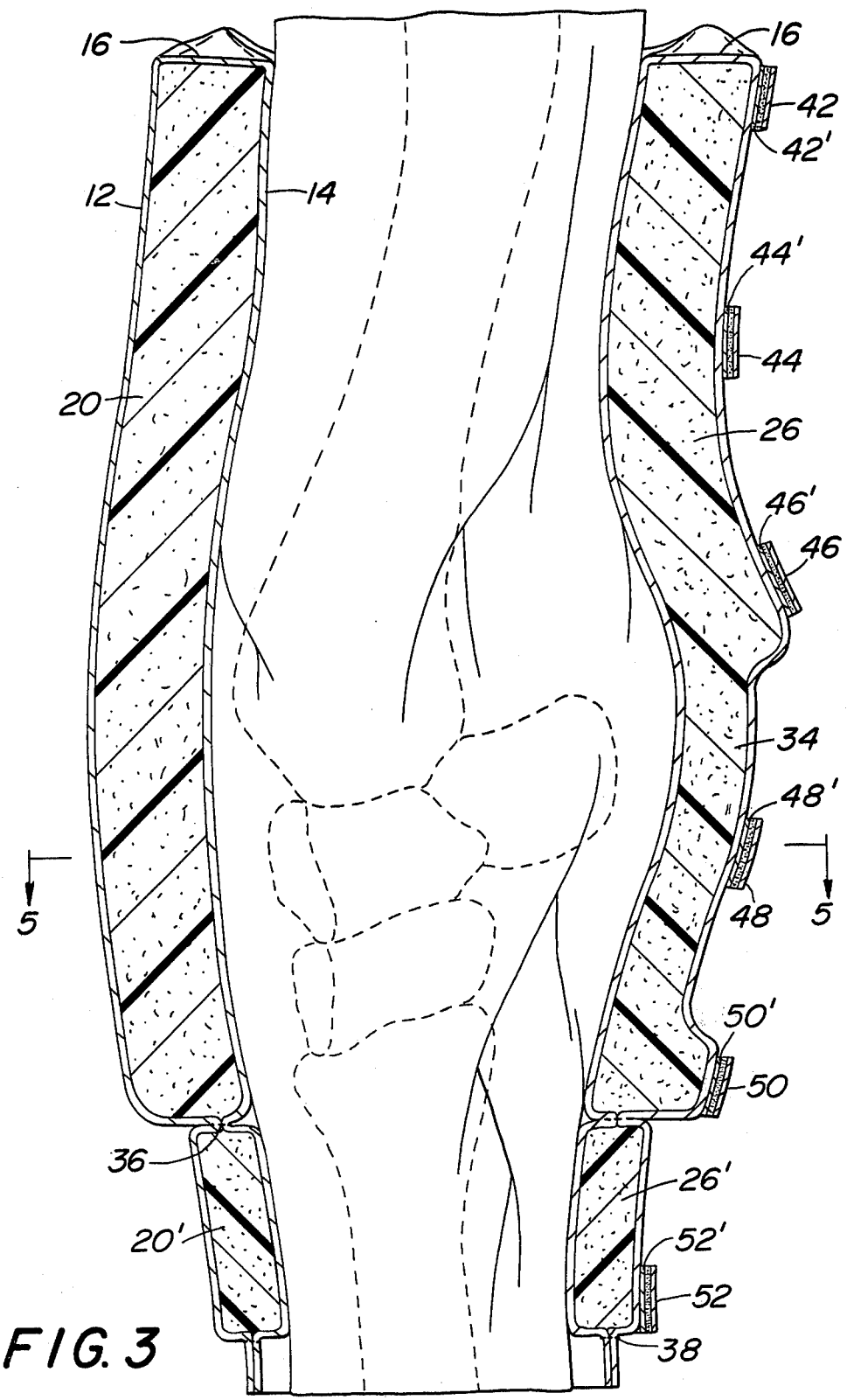
FIG. 3 is a sectional view taken along the line 3—3 in FIG. 2 but on an enlarged scale.
Figure 4:
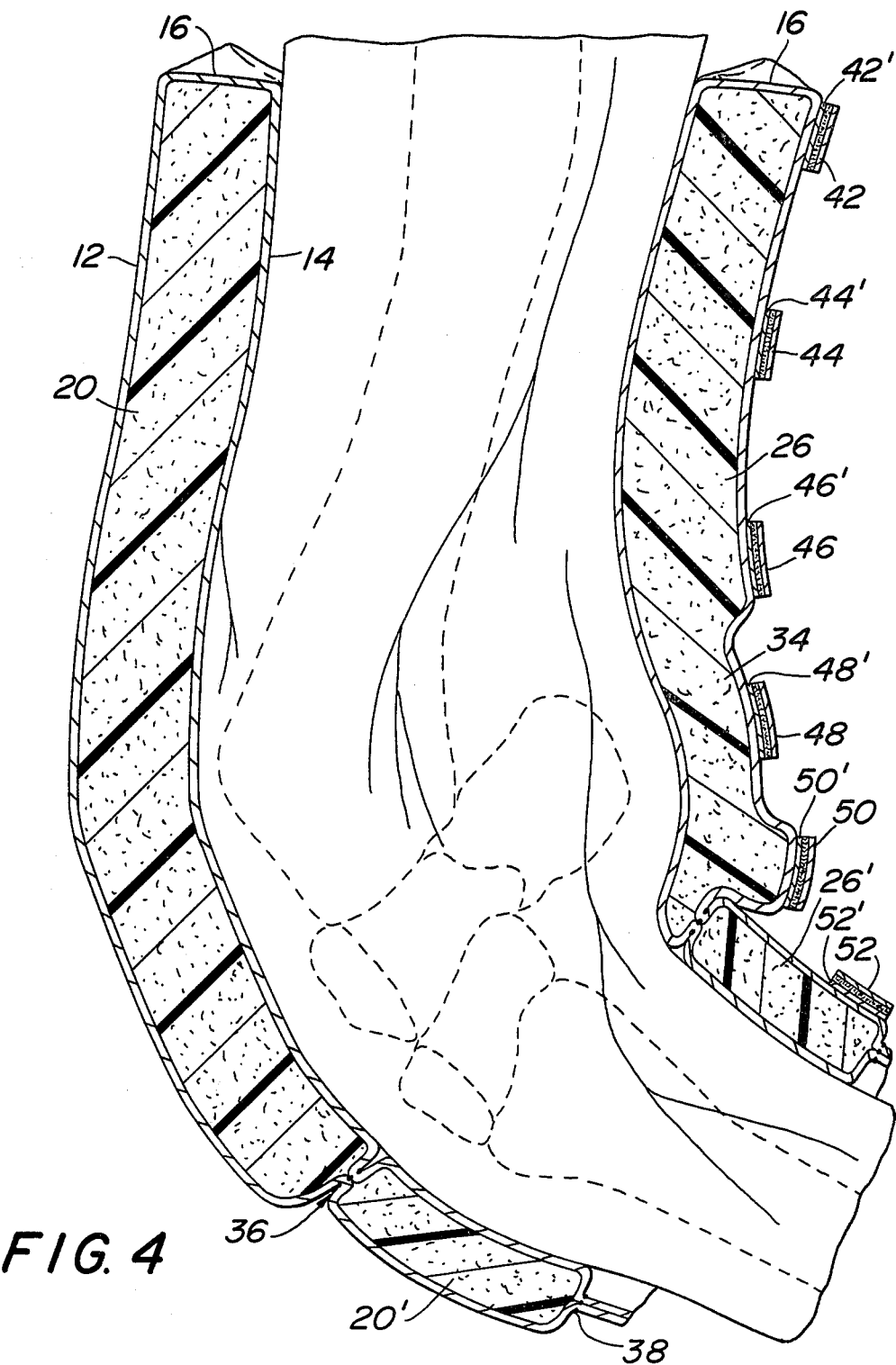
FIG. 4 is a view similar to FIG. 3 but showing the knee bent.

The panels 12 and 14 are stitched horizontally at 36 beneath each of the pads. See FIG. 3. Thus, each of the pads is encased by the bight 16 and the stitching 36 at opposite ends thereof. The pockets continue below the elevation of stitching 36. A pad 18' is aligned with pad 18 and is disposed between stitching 36 and 38. Pad 18' has the same width as pad 18 but is substantially thinner and shorter. Pad 18' preferably has a thickness of approximately ½ the thickness 18. Similar pads 20', 22', 23', 24' and 26' are provided in association with the pads 20, 22, 23, 24 and 26 respectively.

Stitching along opposited side edges of the knee bandage 10 is designated 40. Stitching 41 is applied to the panels 12 and 14 so as to follow the contour of the notches 28 and 30. The side edges and bottom edges of the panels 12 and 14 are provided with an overcast stitch to prevent unravelling. A plurality of straps are stitched at one end to the panels 12 and 14 at a location between pads 18 and 20. As shown in FIG. 1, there are six such straps designated 42, 44, 46, 48, 50 and 52. A greater or lesser number of straps may be utilized. The number of straps illustrated is preferred so as to provide reliability whereby the bandage will not be inadvertently opened. The straps are uniformly spaced from one another except for straps 48 and 50 which are spaced further apart.

Mating strap loops are provided for each of the straps and are identified by corresponding primed numerals. The strap loops have their ends stitched to the panels 12 and 14 and overlie the pad 26. The straps and strap loops are preferably of the Velcro (Trademark) type. The straps and strap loops are positioned in a particular location which corresponds generally to the outside rear quadrant of the knee. In this manner, the horse cannot reach far enough to separate the straps from the strap loops. Also, the location of the strap loops is such that the bandage 10 may be easily applied without danger from being kicked by the horse since the strap loops are on the outside of the leg. The knee bandage 10 as illustrated is for the left front leg. Necessary modifications for a bandage to be used on the right front leg will be apparent to those skilled in the art. In each case, the free end of the straps is adjacent the rear of the knee. See FIG. 5.

The bandage 10 can be used as a post surgical bandage or as a knee protection bandage during shipment of an animal. The bandage can be quickly applied (several minutes versus one half hour for a conventional bandage). The bandage 10 can be applied so as to overlie a poultice plaster, an oil base rubbed onto the knee joint to withdraw fluid from the knee joint (sweat), or a cool pack which is applied to create a cooling sensation for reducing pain and inflamation as well as swelling. The pads 18', 20', 22', 23', 24' and 26' are of reduced thickness so that the bandage 10 may overlie the upper end of a standing bandage which extends from the ankle to the bottom of the knee joint. Bandage 10 does not restrict circulation as is the case with a spider bandage. Thus, the bandage 10 does not restrict circulation nor does it restrict mobility of the horse.

The fabric is preferably 83% nylon and 17% Lycra having 130% stretch in a longitudinal direction and 90% stretch in a transverse direction. The pads are preferably foam polyether. Other materials may be used as desired. The fabric of panels 12 and 14 may be sprayed or otherwise saturated with a horse repellant liquid to provide added protection. The odor and/or taste of the repellant precludes the horse from removing the bandage with his teeth.

The present invention may be embodied in other specific forms without departing from the spirit or essential attributes thereof and, accordingly, reference should be made to the appended claims, rather than to the foregoing specification, as indicating the scope of the invention.

I claim:

1. A knee bandage comprising an enclosure of stretch fabric having stitching defining a plurality of parallel elongated pockets, a pad of foam polymeric plastic material in each pocket, the pads adapted to be on opposite sides of a knee having a zone of reduced cross-sectional area at a location intermediate their ends, at least one of said pads which is adapted to be adjacent a rear surface of the knee having a zone of reduced cross-sectional area, said zones being co-extensive, a plurality of straps along one side edge of the bandage for mating with straps along the opposite side edge.

2. A knee bandage in accordance with claim 1 wherein the reduced cross-sectional area of the pads adapted to be on opposite sides of the knee includes a notch in the pads along the rear edge portions thereof.

3. A knee bandage in accordance with claim 2 wherein said zone of reduced cross-sectional area on the pad adapted to be adjacent a rear surface of the knee is a reduced thickness portion.

4. A knee bandage in accordance with claim 1 wherein said pads have a length of about 30–35 millimeters so as to be sufficient length for use on a horse.

5. A knee bandage in accordance with claim 4 including a discrete second pad in each pocket at the lower end of the bandage, each second pad being substantially thinner than the associated first mentioned pad aligned therewith, said fabric including inner and outer panels connected by a bight at the upper end of the bandage.

6. A knee bandage in accordance with claim 1 wherein the straps along the opposite side edge are strap loops stitched at their ends to the fabric enclosure and overlying an outer face of one of said pads disposed along one side edge of the bandage.

7. A knee bandage comprising an enclosure of stretch fabric having stitching defining a plurality of parallel elongated pockets, a pad of foam polymeric plastic material in each pocket, a pad along a first side edge of the bandage adapted to be along an outside of a knee and an oppositely disposed pad each having a notch along the rear edge portions thereof, a pad adjacent the second side edge of the bandage and adapted to be adjacent a rear surface of the knee having a zone of reduced cross-sectional area, a plurality of straps along said first side edge of the bandage for mating with strap loops along the second side edge.

8. A knee bandage in accordance with claim 7 wherein said pads have a length of about 30–35 millimeters so as to be sufficient length for use on a horse.

9. A knee bandage in accordance with claim 7 including a discrete second pad in each pocket at the lower end of the bandage, each second pad being substantially thinner than the associated first mentioned pad aligned therewith, said fabric including inner and outer panels connected by a bight at the upper end of the bandage.

* * * * *